United States Patent [19]

Ochiai

[11] 4,450,074

[45] * May 22, 1984

[54] CONTROL OF ANAEROBIC FILTER

[75] Inventor: Shinya Ochiai, Corpus Christi, Tex.

[73] Assignee: Celanese Corporation, New York, N.Y.

[*] Notice: The portion of the term of this patent subsequent to Sep. 14, 1999 has been disclaimed.

[21] Appl. No.: 408,088

[22] Filed: Aug. 13, 1982

Related U.S. Application Data

[63] Continuation of Ser. No. 209,813, Nov. 24, 1980, Pat. No. 4,349,435.

[51] Int. Cl.$^3$ .............................................. C02C 1/02
[52] U.S. Cl. .................................. 210/96.1; 210/104
[58] Field of Search ..................... 210/85, 86, 87, 103, 210/104, 110, 120, 218; 324/71 R, 73 AT; 333/70 A, 70 R

[56] References Cited

U.S. PATENT DOCUMENTS 4,349,435  9/1982  Ochiai ................................ 210/96.1

Primary Examiner—John Adee
Attorney, Agent, or Firm—Abner Sheffer

[57] ABSTRACT

The operation of an anaerobic methanogenic filter is controlled by measuring the rates at which oxygen demand (O.D.) is fed to the anaerobic filter and at which methane is generated by the filter, estimating therefrom the O.D. of the effluent of the anaerobic filter and controlling the feed rate to the anaerobic filter in accordance with that estimated value. Also disclosed is a means for eliminating long term bias that may be present in the signals fed from sensors to the circuit used for estimating the value of a variable of a process.

12 Claims, 12 Drawing Figures

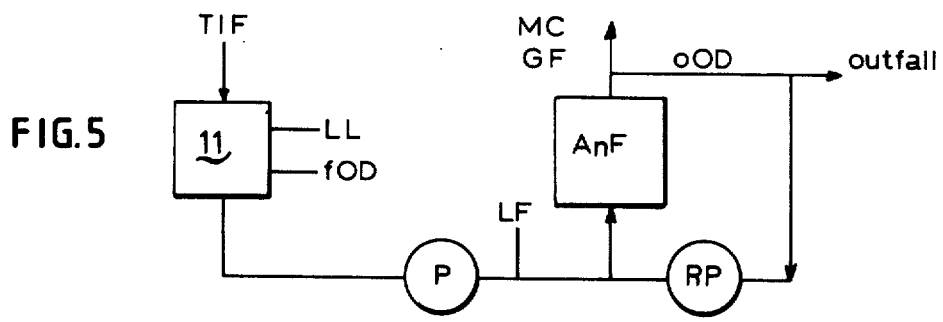
FIG. 5
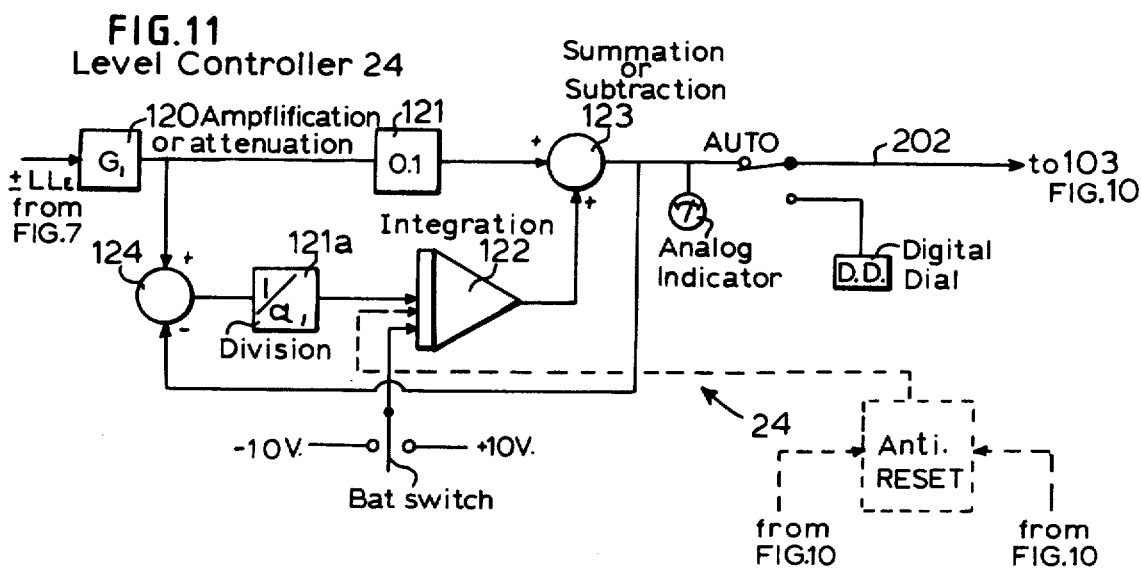
FIG. 11 Level Controller 24
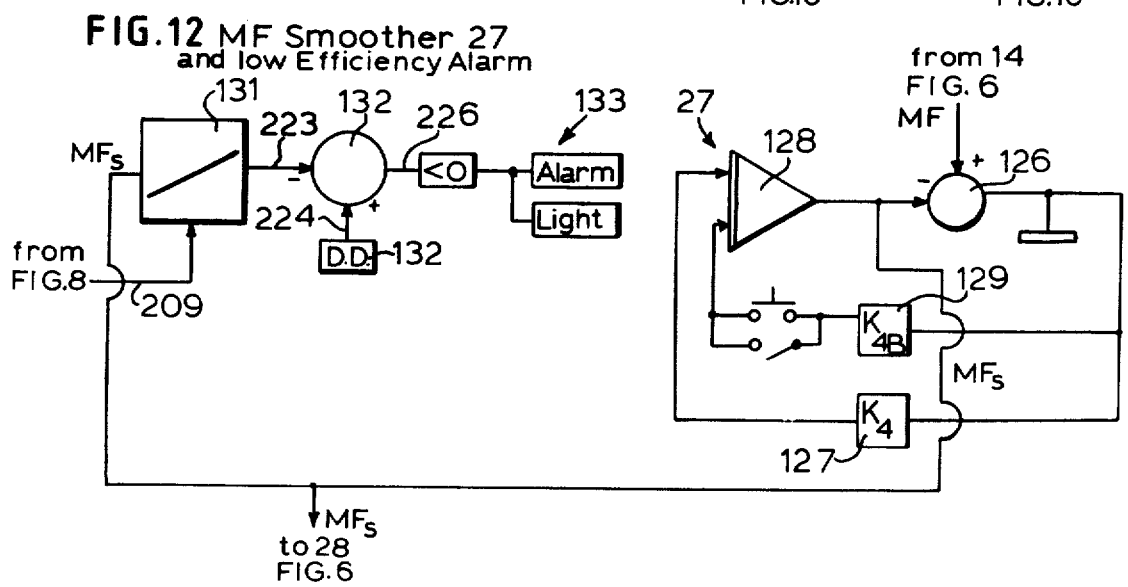
FIG. 12 MF Smoother 27 and low Efficiency Alarm Level Estimator 22
(with Alarm)

fOD Smoother 12

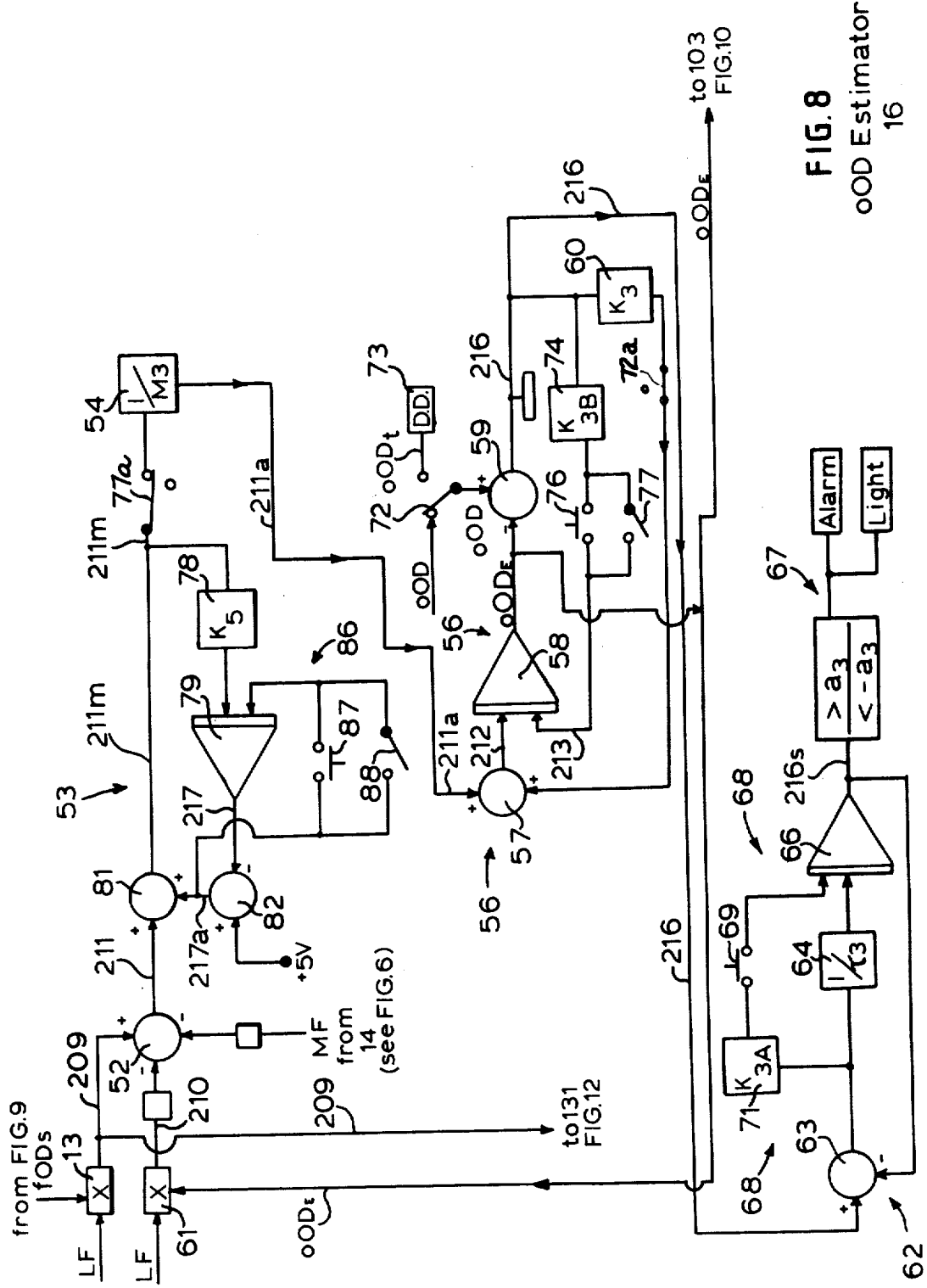

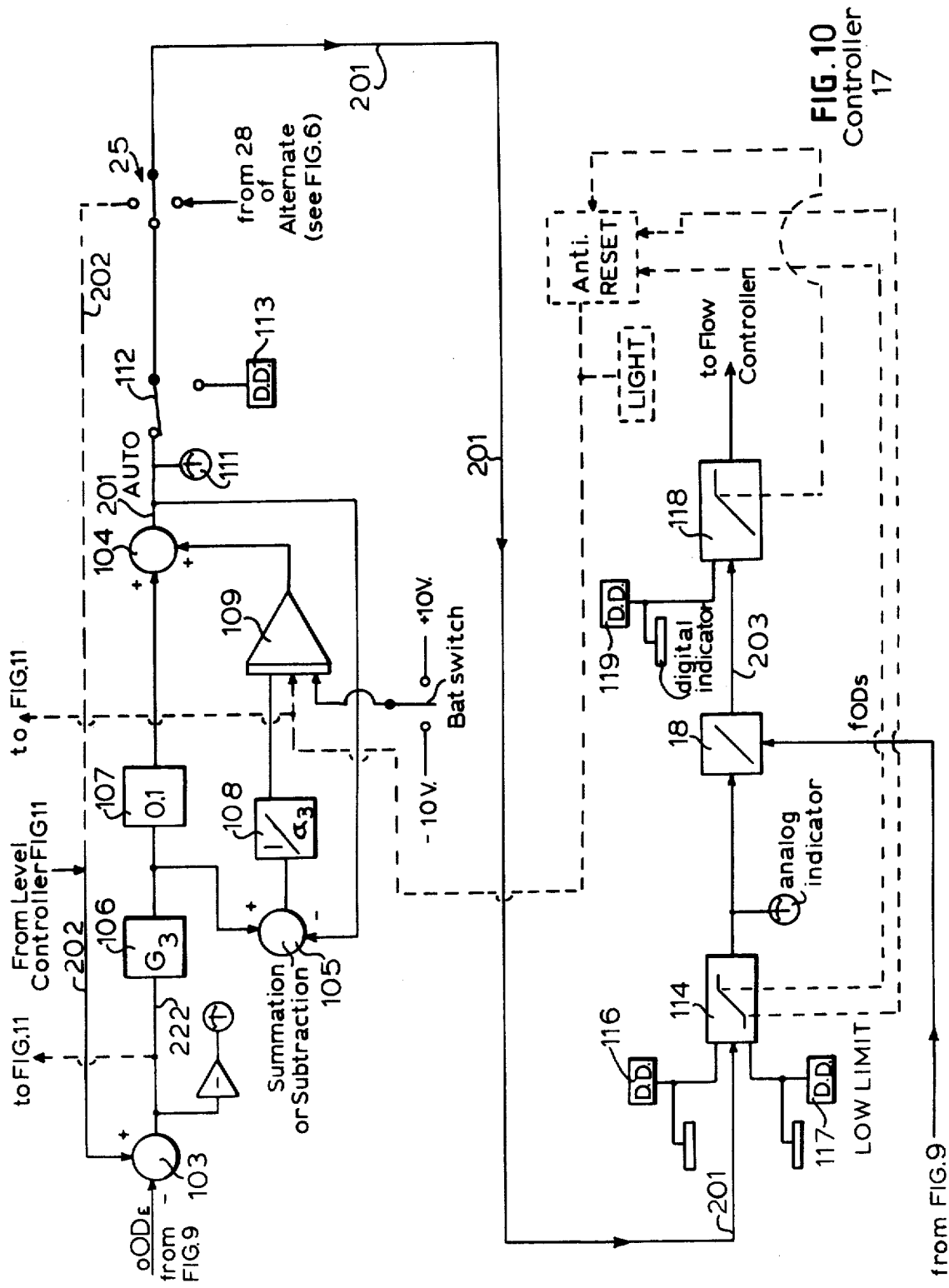

CONTROL OF ANAEROBIC FILTER

This is a continuation of application Ser. No. 209,813, filed Nov. 24, 1980, now U.S. Pat. No. 4,349,435.

One aspect of this invention relates to the control of an anaerobic methanogenic reactor containing a retained backmixed bed of methanogenic bacteria through which aqueous organic waste water is fed upwardly, and in particular to the control of a recycling anaerobic filter.

Another aspect relates to an improvement in the reliability of process control systems in general.

The invention is illustrated in the accompanying drawings in which

FIG. 5 is a schematic flow diagram of a system containing an equalization tank and an anaerobic filter.

Figure 7:
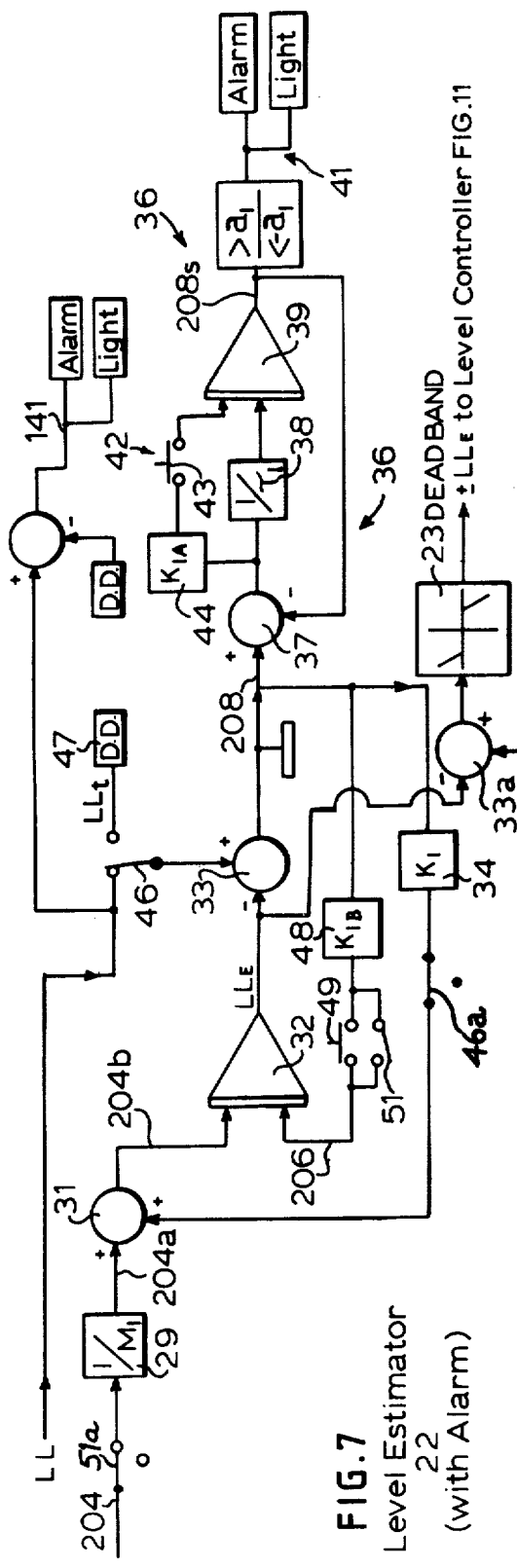
Figure 9:
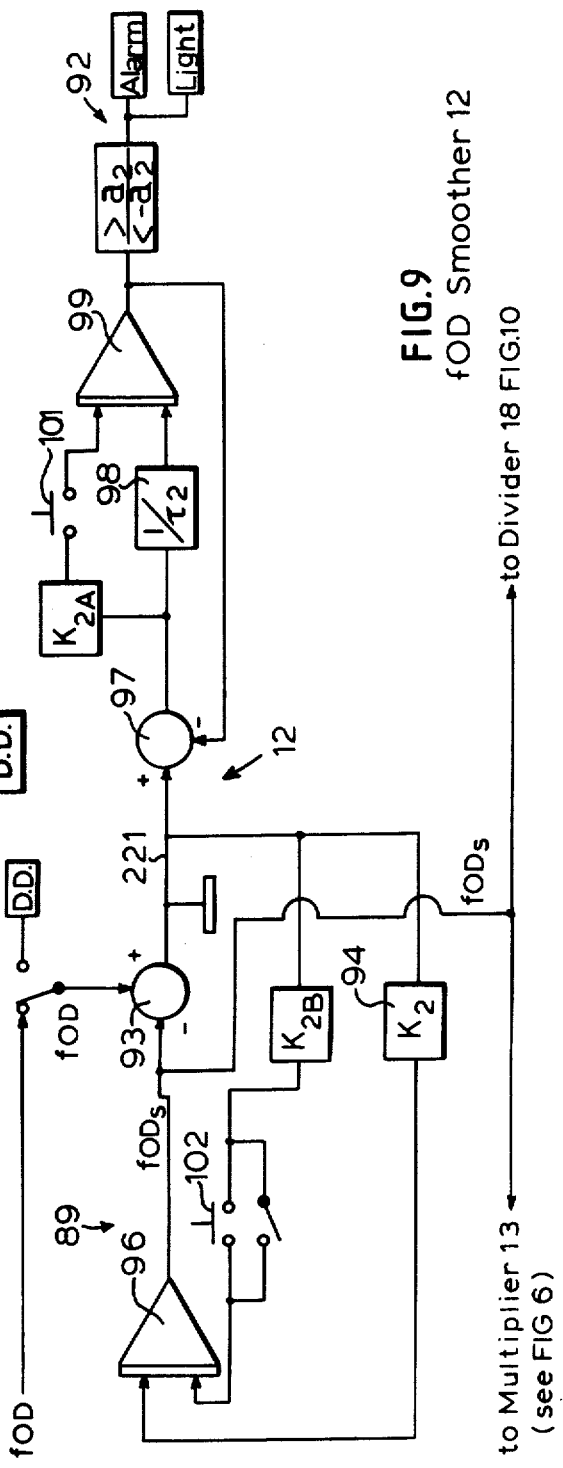

FIGS. 7–12 are schematic circuit diagrams of various units of that control system. FIG. 7 shows a level estimator. FIG. 8 shows an estimator of outfall O.D. FIG. 9 shows a smoother for the feed O.D. signal. FIG. 10 shows a controller. FIG. 11 shows a level controller. FIG. 12 shows a smoother for the methane flow signal and a low efficiency alarm. The symbols for circuit elements are the same throughout these circuit diagrams and are identified in the drawings (not particularly FIGS. 10 and 11) and in the description herein. As noted in FIG. 11 the same symbol is used for an amplifier as for an attenuator.

Figure 1:
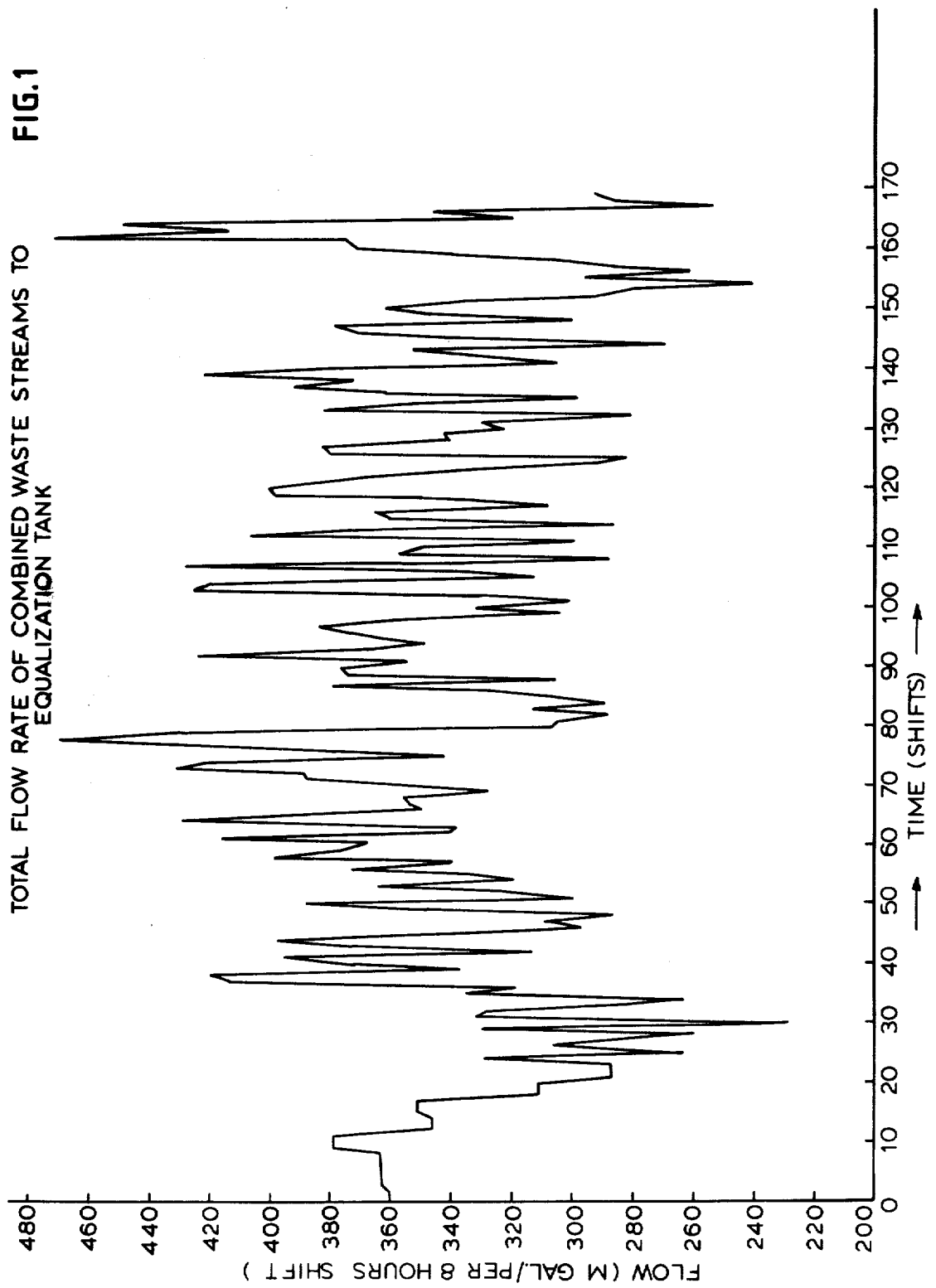
FIG. 1 is a graph showing the volumetric flow of waste streams into the "equalization tank" of a chemical plant over a period of about 8 weeks.
Figure 2:
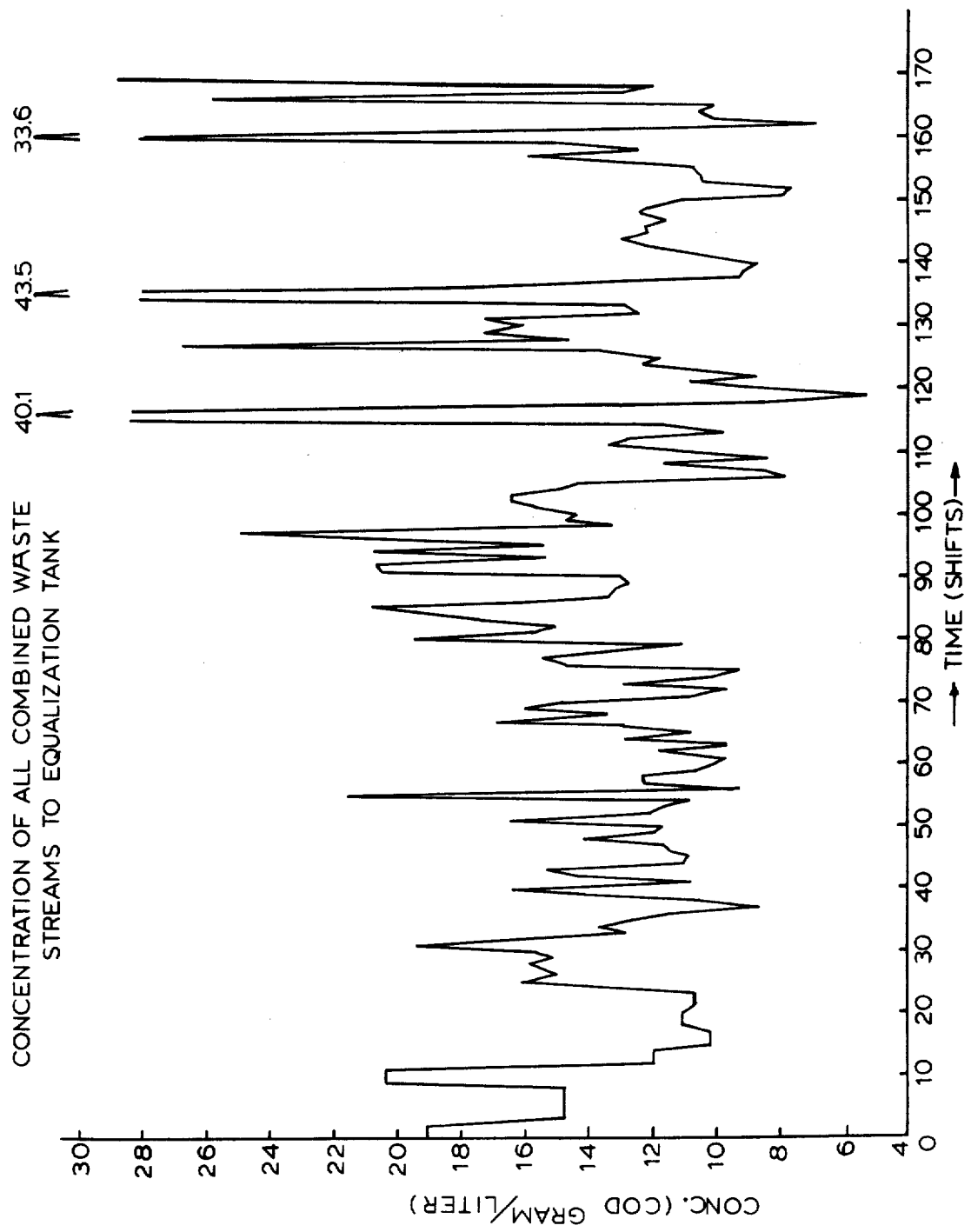
FIG. 2 is a graph showing the average concentration (in terms of grams of C.O.D. per liter) in the material fed to that tank over that same 8 week period.
Figure 3:
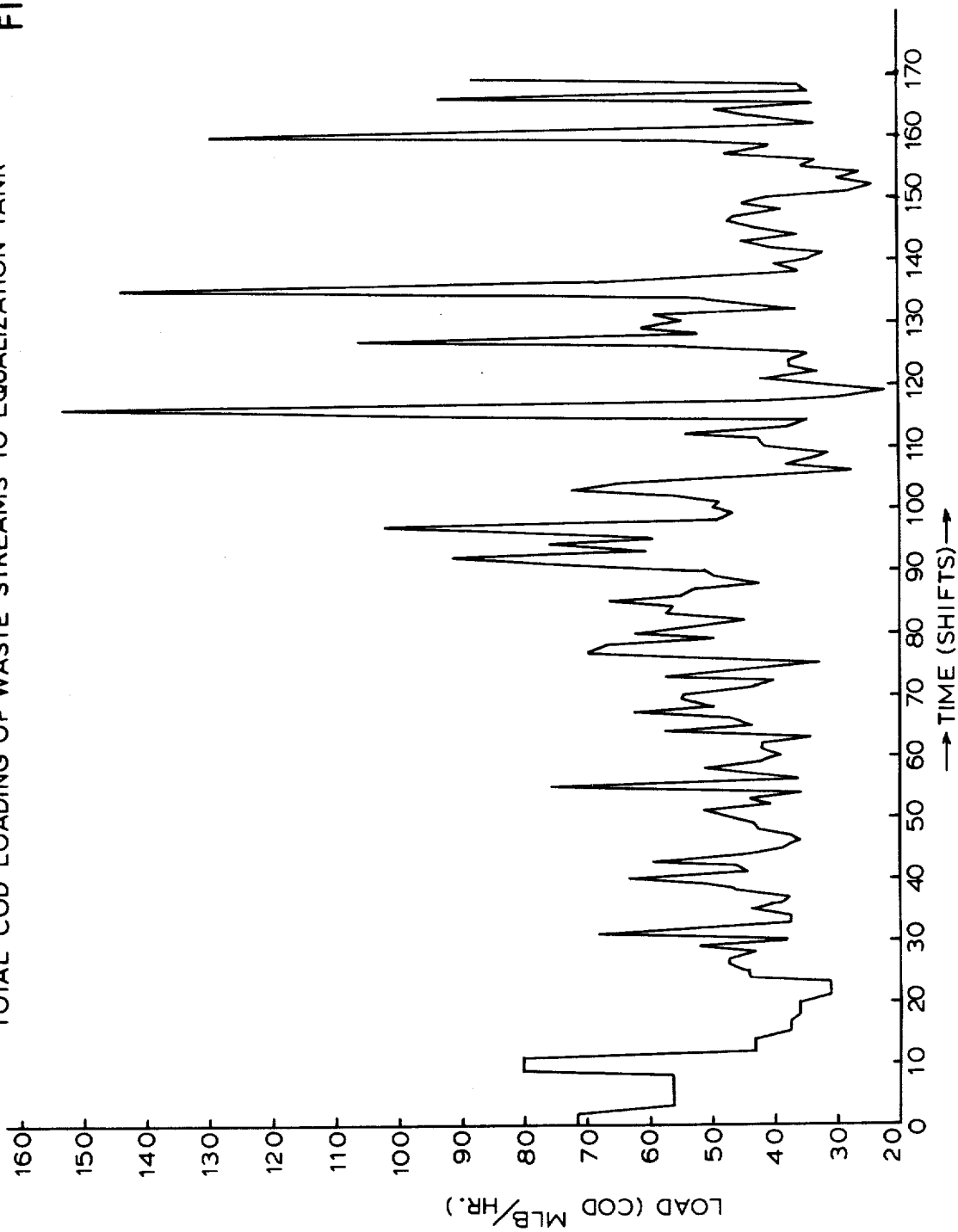
FIG. 3 is a graph showing the total amounts of organics (in terms of lbs. of C.O.D. per hour) fed to that tank over that same 8 week period.

One aspect of this invention relates to the control of the operation of an anaerobic filter which receives an aqueous organic waste stream from a processing plant (such as a petrochemical plant, a food processing plant or a pulp and paper plant). That waste stream may be a composite of various smaller streams from different portions of the plant, of varying concentrations and flow rates, which are fed to an "equalization tank". The volumetric rate and concentration of the total flow into that tank may fluctuate considerably, as can be seen from FIGS. 1, 2 and 3, which show the variations of the total 8-hour flow over a period of about 8 weeks for one petrochemical plant.

In FIG. 5 the term "AnF" designates an anaerobic filter, to which an aqueous organic waste stream is pumped at a controlled rate by a feed pump P from a feed tank (equalization tank) 11. Gas produced in AnF is removed overhead. A portion of the liquid effluent from AnF is removed as outfall and the balance of that liquid effluent is recycled to the lower part of AnF by a recycle pump RP, e.g., by feeding into admixture with the fresh feed. The operation of the anaerobic filter is described, for instance, in the Blay and Witt application Ser. No. 95,915 filed Nov. 19, 1979, and in Witt et al British Pat. No. 1,567,578 published May 14, 1980; the entire enclosures of said applications are incorporated herein by reference.

The control system includes sensors for measuring various parameters and transducers for providing signals representative of those measured parameters. These signals, and the corresponding parameters are listed below:

Signal fOD is representative of the measured value of concentration of oxygen demand ("O.D.", such as total oxygen demand [T.O.D.] or chemical oxygen demand [C.O.D.]) of the contents of the feed tank; this is substantially the same as the O.D. concentration in the fresh feed flowing from tank 11 to AnF. Signal LF is representative of the volumetric rate of flow of that fresh liquid feed. Signal oOD is representative of the measured value of concentration of oxygen demand of the liquid outfall of AnF. In the illustrated embodiment, no separate measurement of the rate of flow of that outfall is made since it is substantially the same as the fresh feed flow rate represented by signal LF. Signal GF is representative of the volumetric rate of flow (reduced to standard conditions of temperature and pressure) of the evolved gas, and signal MC is representative of the methane concentration in that gas.

Signal LL is representative of the measured value of the liquid level (e.g. percent fullness) in the tank 11. Signal TIF (Tank Input Flow) is representative of the measured value of the volumetric input flow into the tank 11.

Figure 6:
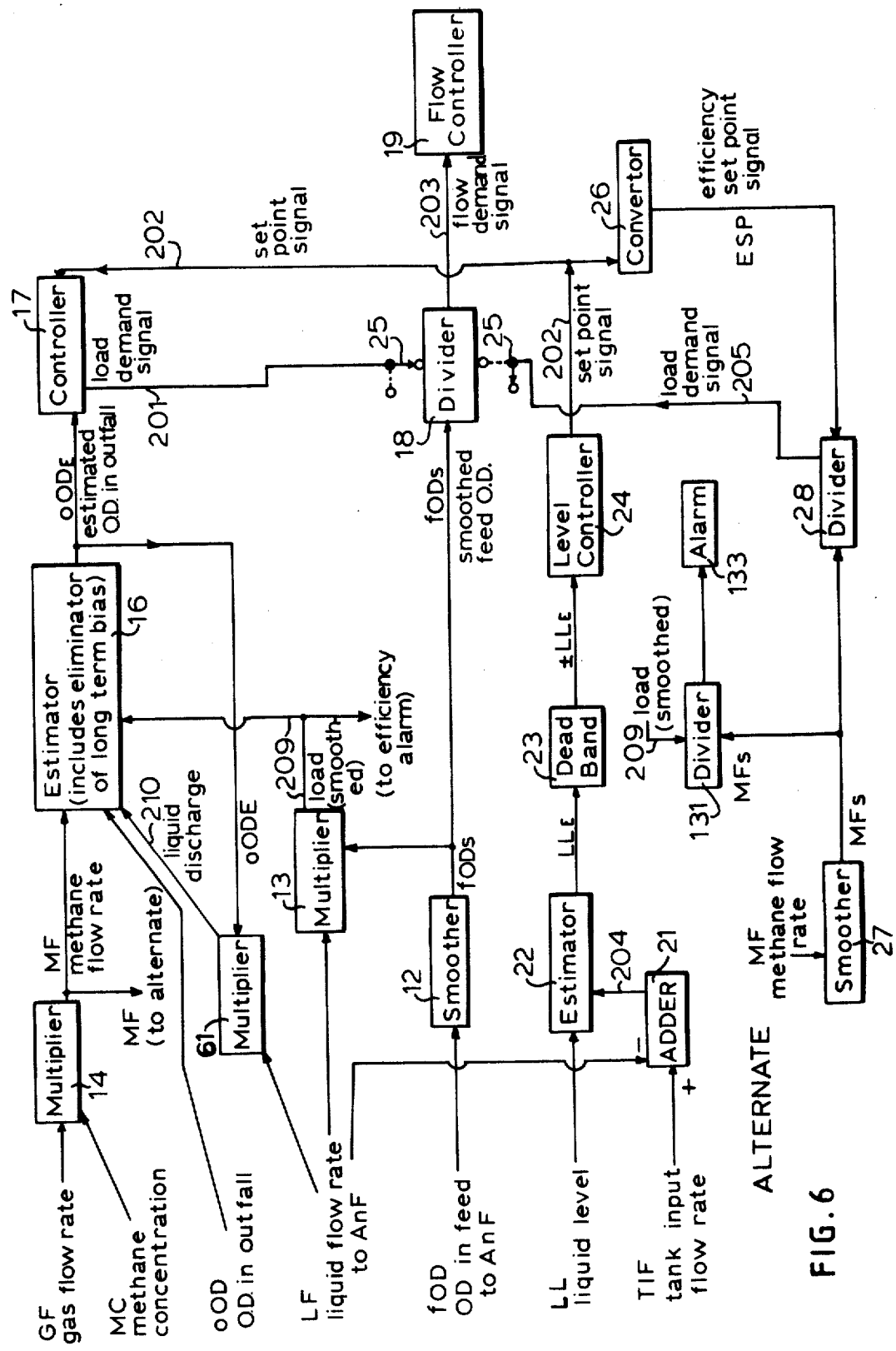
FIG. 6 is a schematic diagram of the elements of a control system for the process illustrated in FIG. 5.

The processing of these signals is outlined in FIG. 6.

Feed O.D. signal fOD acts on a first order lag smoothing circuit 12 having an integration time of several hours (e.g. 16 hours) to give a smoother feed O.D. signal $fOD_S$ which is fed, together with the liquid flow signal LF to a multiplier 13 whose output signal is representative of smoothed rate of flow of O.D. to AnF. The rate of flow of O.D. to AnF is proportional to the "Load" (or "organic load", which is rate of flow of O.D. divided by the [constant] volume of AnF). Thus the signal from multiplier 13 is representative of the Load.

Gas flow signal GF and methane concentration signal MC are fed to a multiplier 14 whose output signal MF is representative of the methane flow rate from AnF, and thus of the rate of removal of O.D. in AnF. (Production of gram mole of methane is equivalent to removal of 64 grams of O.D.).

The methane flow signal MF, the measured outfall O.D. signal oOD, the liquid flow signal LF and the smoothed feed O.D. signal $fOD_S$ are all fed (directly or indirectly) to an estimator 16. That estimator developes an internal signal for a calculated outfall O.D. (based on previous value of outfall O.D. adjusted to take account of the Load of added O.D. minus the rate of removal of O.D. as methane [as indicated by MF]); compares that calculated outfall O.D. with the signal oOD (representing the measured value of outfall O.D. which measured value may be incorrent due, for instance, to instrumental error such as formation of a plug in the sampling line of an on-line O.D. analyzer) and arrives at an estimate of the most likely value of outfall O.D. That estimated value, represented by signal $oOD_e$ is fed to a main controller indicated generally as 17 which, in turn, provides a load of the feed to AnF. Thus the feed rate is increased when the $oOD_E$ is below the desired set point and the feed rate is decreased when the $oOD_E$ is above that set point.

The system provides a cross-check on the information provided by the sensors. It does not wholly rely on the measured value of outfall OD. which could be erroneous. Preferably it does not wholly rely on a calculated value, which is dependent on accurate measurement of, for instance, flow rate. The preferred system relies on only relatively reliable or repeatable measurements, such as flow rate signals of high repeatability and (see discussion of high pass filter, below) values of oOD that are not subject to integration with respect to time. The system includes an alarm (described below) that is actuated when the difference between the calculated and measured values is greater than some predetermined amount. In response to the alarm the operator manually disconnects the system from the oOD sensor, takes a sample of the outfall and makes an independent measurement of outfall OD (or in his discretion, based on experience with the operation of this system in particular situation, relies on an earlier such independent measurement) and re-sets the instrument to insert the "true" value for the outfall OD concentration.

In the controller 17 the estimated outfall O.D. signal $oOD_E$ is compared with a predetermined set point signal and the resulting difference (or "error") signal is processed according to lead lag control logic to give a Load demand signal 201 which is sent to a divider 18 where it is divided by the smoothed feed signal $fOD_S$ to give a liquid flow demand signal 203 which is fed to a flow controller 19 which in turn acts on the speed control of pump P or on another suitable flow regulating device acting on the liquid in the feed conduit.

The size of the feed tank 11 is advantageously as small as possible, for economic reasons; for instance, its capacity may be equal to, say, one day's average total flow (i.e. TIF×24 hrs). To avoid or limit the need to divert (from the tank) all or part of the plant waste stream, there is provision for controlling the liquid flow rate from the tank in accordance with the liquid level therein. To that end, the set point signal 202 which is fed to controller 17 is made partly dependent on the liquid level in the feed tank 11. That is, when that level rises above a pre-determined deadband the set point is raised, which has the effect of increasing the rate of feed to the anaerobic filter. Conversely, when the liquid level falls below the deadband the set point is lowered; thus the feed rate to the anaerobic filter is decreased when, because of the relatively small amount of material in the tank, that material will not be as effective in diluting any surge of highly concentrated toxic materials that may be introduced into the tank.

The manner in which the liquid level influences the set point is as follows: The Signal TIF (representative of the measured tank input flow rate) and the signal LF (representative of the liquid flow from the tank) are fed to an adder 21 whose output signal 204 is the difference between TIF and LF; this flow difference signal is fed, together with signal LL (representative of the measured liquid level in the tank) to an estimator 22 which generates an estimated liquid level signal $LL_E$. The $LL_E$ signal in turn passes to a dead band device 23 to generate a signal $\pm LL_E$ which represents the amount by which the estimated liquid level signal is above or below a predetermined dead band. This signal $\pm LL_E$ acts on a level controller 24 where it is processed according to lead-lag control logic to give the set point signal 202 that is fed to the main controller 17.

In the illustrated embodiment there is also provided an alternate control system, which may be substituted (by manually controlled switch 25) for the control system described above and which may be particularly useful in the period when the AnF is being started up or being brought to a desired high capacity. This alternate system is of the type disclosed in the copending patent application of Blay and Witt Ser No. 95,915 filed Nov. 19, 1979, and involves regulating the flow of feed O.D. to maintain a predetermined O.D. removal efficiency. Since the efficiency equals the rate of removal of O.D. divided by the rate of feed of O.D., and the rate of removal of O.D. is proportional to the methane production rate, one can determine the desired O.D. feed rate by dividing a signal representative of the methane flow rate by a signal ESP representing the predetermined efficiency.

The set point for the efficiency is varied so as to reflect the liquid level in the tank; when the level is above the predetermined dead band the efficiency is set at a lower level (i.e. the relative rate of feed of OD is higher) and vice versa. To that end, the set point signal 202 generated by the level controller 24 is used, after appropriate conversion in a converter 26, as the efficiency set point signal ESP. The methane flow signal MF is passed to a smoother 27 to give a smoothed methane flow signal $MF_S$. The latter is divided by the efficiency set point signal ESP in divider 28 to give a load demand signal 205 which is fed to the divider 18 when this alternate system is in operation.

Thus the feed rate to the anaerobic filter is increased when the efficiency is above the predetermined efficiency set point, and vice versa.

Turning now to the schematic circuit diagram for the level estimator (FIG. 7) the flow difference signal 204 (from adder 21) represents the percent change in volume of the tank per unit time. While signal 204 may be generated as the numerical value of a flow rate (e.g. in gallons or m³ per minute), dividing that flow rate by a constant (i.e. the volume of tank 11) gives a signal 204a for the numerical value of percent change of tank volume per minute; in the illustrated embodiment such division by a constant is effected by attenuator 29. The signal 204a is modified in adder 31 (as described below) to form a signal 204b which is fed to an integrator 32 which has been preset, by a signal 206 for the then-existing level (percent fullness) of the tank. Thus the output of the integrator 32 is a signal $LL_E$ representing an instantaneous estimate of the level of the tank. That signal $LL_E$ is subtracted from the signal LL in an adder 33 and the resulting signal 208 for the difference between LL and $LL_E$ is then fed back through an attenuator 34 to adder 31 to modify the signal 204a; this feedback inhibits small errors in flow measurements from building up and affecting the output of integrator 32.

The illustrated embodiment includes means for actuating an alarm when there is an undue and persistent difference between the signals for estimated and measured values of liquid level. To that end the signal 208 is fed to a first order lag filtering circuit indicated generally by reference numeral 36 which serves to filter out any short duration "spikes" in signal 208, giving a smoothed signal 208s; this circuit 36 is of conventional type and comprises an adder 37, an attenuator 38, and an integrator 39 having a feedback connection to the adder 37. The alarm 41 is pre-set to be actuated when the magnitude of signal 208s (whether positive or negative) is greater than a predetermined value. For shutting off the alarm 41 manually there is a circuit 42 (including a momentary contact ("m.c.") switch 43 and an amplifier 44) through which the integrator 39 can be discharged. For correcting the situation indicated by the alarm 41, means are provided for the operator to insert the true value of the tank level into the system (e.g. when there is a malfunction of the level measuring sensor, which may be caused by a solid plug in the level sensor). Such correcting means includes a switch 46 to disconnect the measured level signal from the system and to connect signal $LL_t$ (generated e.g. from a digital dial 47) and also a re-set circuit to connect difference signal 208 to integrator 32 through an amplifier 48 having a relatively high gain (as compared to the very low gain attenuator 34) and through an m.c. switch 49 (or, alternatively, through a switch 51 which may be on a supervisor's control panel) so that by operating m.c. switch 49 the estimated value very quickly becomes equal to the true value. There is a switch 51a to disconnect the flow difference signal 204 from the level estimator circuit. Switches 43, 49 and 51a are controlled and actuated simultaneously by a single push button so that when switches 43 and 49 are closed switch 51a is opened.

Associated with the deadband device 23 is an adder 33a at which the signal $LL_E$ is subtracted from a level set point signal generated at a manually variable digital dial.

A schematic circuit diagram for the outfall OD estimator 16 is shown in FIG. 8. At adder 52 (upper left of FIG. 8) the net output rate of the anaerobic filter (i.e. the sum of signal 210, which is representative of the liquid O.D. discharge rate, plus signal MF which is representative of the methane flow rate) is subtracted from the net input rate (i.e signal 209 which is representative of the load), so that the resulting signal 211 represents the rate of change of O.D. material in the anaerobic filter. Of course one or more of these signals may need to be passed through a suitable amplifier or attenuator (as shown in FIG. 8) where the signal is multiplied by an appropriate constant to insure that all numerical values are in the same units (e.g. grams COD per minute). The output signal 211 of adder 52 is passed through a high pass filter 53 (described more fully below) and the resulting modified signal 211m is passed through an attenuator 54 where its numerical value is divided by a constant, namely the amount of liquid contained in the anaerobic filter (and associated piping) thus giving a signal 211a for the estimated change in concentration of O.D. in the anaerobic filter. That signal 211a is fed to a circuit 56 of the same type as the estimator circuit shown in FIG. 7, discussed above. That is, it is fed to an adder 57 (described below) giving signal 212 which is fed to an integrator 58 which has been pre-set, by a signal 213, for the then-existing O.D. concentration in the anaerobic filter, so that the output signal $oOD_E$ of integrator 58 represents an instantaneous estimate of the O.D. concentration in the anaerobic filter. The signal $oOD_E$ is subtracted from the signal oOD in an adder 59 and the resulting signal 216 the difference between oOD and $oOD_E$ is then feed back through plifier (i.e., attenuator) 60 to adder 57 to modify the signal 211a; this feedback inhibits small errors in measurements from building up and affecting the output of integrator 58. The signal 210 (which is representative of the liquid O.D. discharge rate and is, as mentioned above, fed to adder 52) is generated at a multiplier 61 which receives the signals $oOD_E$ and LF.

The illustrated embodiment includes means for actuating an alarm when there is an undue and persistent difference between the signals for estimated and measured values of outfall OD concentration and for manually correcting the system. This is similar to the arrangement shown in FIG. 7 described above. The signal 216 is fed to a first order lag filtering circuit indicated generally by reference numeral 62 which serves to filter out any "spikes" in signal 216, giving a smoothed signal 216s; this circuit 62 is of conventional type and comprises an adder 63, an attenuator 64 and an integrator 66 having a feedback connection to the adder 63). The alarm 67 is preset to be actuated when the magnitude of signal 216s (whether positive or negative) is greater than a predetermined value. For shutting off the alarm manually there is a circuit 68 (including an m.c. switch 69 and an amplifier 71) through which the integrator can be discharged. For correcting the situation indicated by the alarm, means are provided for the operator to insert the true value of the outfall O.D. concenration into the system (e.g. when there is a malfunction of the outfall O.D. measuring sensor). Such correcting means includes a switch 72 to disconnect the measured outfall O.D. signal from the system and to connect instead a correct signal $oOD_t$ (generated e.g. from a digital dial 73) and also a re-set circuit to connect difference signal 216 to integrator 58 through an amplifier 74 having a relatively high gain (as compared to the very low gain of attenuator 60) and through an m.c. switch 76 (or, alternatively, through a switch 77 which may be on a supervisor's control panel) so that by operating switch 76 the estimated value quickly becomes equal to the true value. There is a switch 77a to disconnect input signal 211 from the estimator circuit. Switches 69, 76 and 77a are controlled (and actuated simultaneously) by a single push button so that when switches 69 and 76 are closed switch 77a is opened.

The high pass filter 53 comprises a feed-back loop including a very low gain attenuator 78 and an integrator 79 feeding to an adder 81 where the output signal 217 of the integrator (modified, in the illustrated embodiment, by a predetermined fixed bias) is subtracted from the input signal 211. The signal 217 is a moving average value of the output of adder averaged over a long term so that signal 211m from adder 81 represents the difference (positive or negative) between the signal 211 and that moving average value. If there is no consistent bias (error) in the signals from the sensors the long term moving average signal 217 will be zero and signal 211 will not be modified at adder 81. But if there is some (unknown) consistent bias in one or more of the sensors and thus in signal 211, the moving average 217 will drift (gradually) in one direction and the effect of the bias will thus be cancelled out at adder 81 and will not appear in signal 211m. In the absence of the high pass filter 53 a small constant bias would be integrated with respect to time over a long period and would produce a significant error in the value of $oOD_E$.

In a preferred construction the integrator 79 of the high pass filter is a clock controlled digital integrator, as described below. The sign of the output signed 217 of that particular device is only in one direction (negative or positive) and cannot vary from negative to positive through a zero (which zero corresponds to the absence of long term bias). To correct for this, a fixed bias is added to the signal 217 at an adder 82 giving a resulting signal 217a that is fed to adder 81. Thus if signal 217 varies from zero to $-10$ volts (the $-5$ volt signal corresponding to absence of long term bias) and the fixed bias added at 82 is $+5$ volts, the resulting signal 217a will vary from +5 to −5 volts and the zero volt signal 217a will correspond to an absence of long term bias. The magnitude of the fixed bias is chosen so as to be greater than the magnitude of any expected long term bias from the sensors.

To discharge the integrator 79 manually there is a circuit 86 including an m.c. switch 87 and alternative panel switch 88.

The smoother 12 shown in FIG. 9 comprises a conventional first order lag smoothing circuit 89. It also compares (at adder 93) the measured feed OD signal fOD with the smoothed signal fOD$_s$; if the difference (signal 221) between fOD and fOD$_s$ is unduly large, and is sustained (i.e. is not a short-duration spike) an alarm is actuated. The means for actuating the alarm and for manually correcting the system is similar to the arrangement shown in FIG. 7 described above.

More particularly, the smoothing circuit includes an adder 93 and low gain amplifier (i.e. attenuator) 94 and an integrator 96. The difference signal 221 is fed to a first order lag filtering circuit comprising an adder 97, an amplifier 98 and an integrator 99 having a feedback connection to the adder 97. The alarm 92 and m.c. switches 102 and 102 operate in the same manner as the corresponding elements in FIG. 7 (and in FIG. 8). Switches 101 and 102 are controlled (and actuated simultaneously) by a single push button.

The controller 17 (FIG. 10) incorporates known lead-lag control logic. It includes adders 103, 104, and 105, amplifier 106 and attenuators 107 and 108 and integrator 109, and it operates according to the known formula (expressed in terms of the Laplace variable "s"):

$$m(s)e\frac{G_3(1 + 0.1\alpha_3 s)}{1 + \alpha_3 s} e(s)$$

where m(s) is the frequency characteristic of the output signal (load demand signal 201) of the controller, e(s) is the frequency characteristic of the "error" (i.e. signal 222) and $G_3$, 0.1 and $1/\alpha_3$ are the gain factors of the amplifier 106 and attenuators 107 and 108 respectively. The error signal 222 is generated at adder 103; as previously indicated, it is the arithmetical difference between the signal oOD$_E$ (representative of estimated O.D. concentration in the outfall) and the set point signal 202 from the level controller 24.

For manual control (described below) of the load demand signal 201 there is a visible indicator 111 to show the value of the output signal of controller 17 and a switch 112 to disconnect the automatic control and to substitute a load demand signal supplied from a manually operated digital dial 113.

The load demand signal 201 preferably passes through a limiter 114 whose characteristic curve is indicated thereon in the drawing. This eliminates the portion of the signal above a predetermined maximum (which is manually set at digital dial 116) and below a predetermined minimum (which is manually set at digital dial 117). The maximum and minimum load limit settings for limiter 114 are determined by experience and judgment based on the observed behavior of the particular anaerobic filter in the particular plant. Minimum load limit is superfluous when the control system is being operated according to load demand signal 201 (in response to value of outfall OD) but it is advantageous when the control system is being operated according to load demand signal 205 (in response to value of efficiency), in the latter case it moderates the rapid drop in loading that can occur during operation in that mode.

The flow demand signal 203 passes through a high limit device 118, which eliminates any signal values above a predetermined maximum (set manually at digital dial 119), thus avoiding the possibility that the volumetric rate of flow to the anaerobic filter will be so high as to decrease the recycle ratio unduly (e.g. when one uses a system in which the recycle pump RP (FIG. 6) is driven at a constant rate) or so high as to have an adverse physical effect on the operation of the anaerobic filter.

The construction of level controller 24 (FIG. 11) is similar to that of controller 17. It comprises amplifier 120 and attenuators 121, 121a (having gain factors $G_1$, 0.1 and $1/\alpha_1$ respectively) integrator 122 and adders 123, 124 and it operates according to the formula given above (with $G_1$ and $1/\alpha_1$ substituted for $G_3$ and $1/\alpha_3$, respectively). The error signal fed to the level controller 34 is the signal $\pm LL_E$ from the dead band unit 23.

The construction of the smoother 27 (FIG. 12) for the methane flow rate signal MF is similar to that of the smoother 12. It comprises an adder 126, an attenuator 127 and an integrator 128, together with a push button- and switch-controlled circuit including a high gain amplifier 129.

The system includes means for activating an alarm when the efficiency of the anaerobic filter drops below a predetermined level. The smoothed Load signal 209 and the smoothed methane flow rate signal MF$_s$ are fed to a divider 131. From the resulting smoothed efficiency signal 223 there is subtracted (in adder 132) the predetermined efficiency set point signal 224 from a manually set digital dial 132; if the resulting signal 226 is less than zero the alarm 133 is activated. The operator will then throw switch 112 (FIG. 10) to disconnect the automatic control and bring the flow to the anaerobic filter under manual control. He will set the control signal (at dial 113, FIG. 10) at a lower value than that of the visible automatic signal shown by indicator 111, thus lowering the flow to (and thus the load on) the anaerobic filter; the choice of the particular lower value will depend on the operator's informed judgment. This lowering of the flow rate naturally results in an immediate decrease in the unsmoothed signal LF and thus a corresponding immediate decrease in signal 209, thus immediately deactivating the alarm 133. If, despite this change, the alarm is subsequently reactivated by a further drop in efficiency the operator will then manually set the control signal at a still lower value, and so on until the alarm stops.

When the level in the tank 11 drops to some predetermined lower limit the flow from tank 11 to the anaerobic filter is shut off automatically (by conventional means, not shown) until the level rises above that limit. Shown in FIG. 7 is an alarm 141 which is actuated, to warn the operator when the level in the tank has dropped to slightly above that lower limit. As can be seen in FIG. 10, the system may also include the option of bypassing the controller 17, by feeding the set point signal 202 from the level controller 24 directly to switch 25 in which event the flow is controlled by the level controller entirely.

On-line sensors for OD are often not highly reliable. The system includes an optional mode of operation in which an on-line oOD sensor is not used or is disconnected. In applying that optional mode, reliance may be placed on intermittent laboratory analyses for values of $oOD$, e.g. analyses taken at, say, 4, 8 or 12 hour intervals. Thus the operator may move switch 72 (FIG. 8) to the right and set dial 73 to the value of oOD obtained by the laboratory analysis (thus generating a signal $oOD_t$) and push the button 76 (which, as explained earlier makes $oOD_E$ equal to $oOD_t$) and then release that push button whereby the latter returns to its original open position. The circuit includes a switch 72a which is operated by movement of switch 72 so that when switch 72 is in the right hand position switch 72a is open; this disconnects the feedback to adder 57 making signal 212 the same as signal 211a. Accordingly in the periods (of any 12 hours each) between manual insertions of $oOD_t$ values, the manually inserted signal $oOD_E$ will be continuously modified by the (integrated) algebraic slum of the OD input ($LF \times fOD_s$) minus the OD Output represented by MF (methane flow) and minus the OD output in the outfall ($LF \times oOD_E$), with long term bias eliminated. The resulting $oOD_E$ signal will be fed to the controller 17 (FIG. 10) in the manner as described earlier.

A similar arrangement may be used in the level estimator 22 (FIG. 7) so that instead of using an on-line level sensor, an intermittently measured value of the level may be inserted (at dial 47, generating signal $LL_t$). Here there is a switch 46a controlled by switch 46 so that when adder 33 is connected to dial 47 the feedback circuit containing amplifier 34 is disconnected. The operator dials the value the true level at 47, moves switch 46 to the right and temporarily (e.g. for one or two seconds) depresses m.c. switch 49. The signal $LL_E$ thereafter has the value of $LL_t$ continuously modified by the (integrated) algebraic sum of TIF and LF (from adder 31, integrated at 32). If the operator believes that there may be a longterm bias in signal 204, the connection between amplifier 34 and adder 31 should not be opened (i.e. there should be no switch 46a or that switch should be operatively disconnected from switch 46) so that the feedback circuit through amplifier 34 can remain effective to modify signal 204a.

The "constants" for the illustrated circuit elements are chosen in a manner known to those skilled in the control art, based on simulation of the overall process involved in the anaerobic filter as represented by linear differential equations (taking account of such factors as the historical, statistical variations in the rates of flow and O.D. levels of the waste stream from the processing plant, possible inaccuracies in the sensors, etc.). Computer programs for operating on these differential equations (e.g. using the mathematical approach known as Kalman filtering technique) to provide optimal values for some of the constants (e.g. those shown on the drawings as K2, K3 and K4) are available, as from Massachusetts Institute of Technology; these constants may also be determined by engineering judgment.

The choice of amplifier and attenuator gain values will naturally depend on the parameters of the process. Take, for instance, a process in which the parameters are as follows: typical average residence time ($T_t$) in the equalization tank (i.e., a typical working volume of liquid in the tank divided by a typical rate of flow into the tank) about 11 hrs; typical average residence time ($T_f$) in the anaerobic filter about 18 hrs; average TOD in feed 14 g/l; desired TOD in outfall 1.7 g/l. For such a process, calculations indicate that the amplifiers and attenuators should have values such that the integration times for the various integrators are approximately as follows: integrator 32, 16 hours (i.e. about 1.4 $T_t$); integrator 96, 16 hours (again about 1.4 $T_t$); integrator 58, 6 hours (i.e. about 0.34 $T_f$); integrator 128, 5 hours (about 0.28 $T_f$) or less, e.g. 1 or 2 hours; integrator 79, 2 days (about 2.7 $T_f$); integrator 122, 25 hours (about 2.1 $T_t$); integrator 109, 10 hours (about 0.57 $T_f$). The integration times are functions of the values of the amplifiers and attenuators in the circuits (such as 34 for integrator 32); these amplifiers and attenuators are of the conventional manually variable type so that the integration times may be adjusted to modify the operation of the control system.

Theoretically, in a complete treatment of the system, the output of estimator 16 would be an input to smoother 12 and to smoother 27, the output of smoother 27 would be an input to estimator 16 and to smoother 12, and the output of smoother 12 would be an input to smoother 27. However study and calculation has shown that these items have only a small effect and they are therefore not included in the preferred control circuit to avoid unnecessary complications in design and operation.

The integrator 79 of the high pass filter 53 (FIG. 8) is a clock-controlled digital integrator comprising an analog-to-digital converter, a shift register, an up/down counter and a digital-to-analog converter, with time sequencing circuitry to provide timed pulses, each of which serves as a shift command to send the information from the shift register to the up/down counter. By controlling the timing of the pulses the integration rate is controlled; the higher the frequency of the pulses, the faster the rate of integration. Typically the timing of the pulses is slower than 30 pulses per minute, e.g. 20 pulses or 10 pulses or 1 pulse per minute. The integration time of the device may, for instance, be on the order of a day or more. If available a general purpose digital computer may be programmed to serve this long term integrating function.

Figure 4:
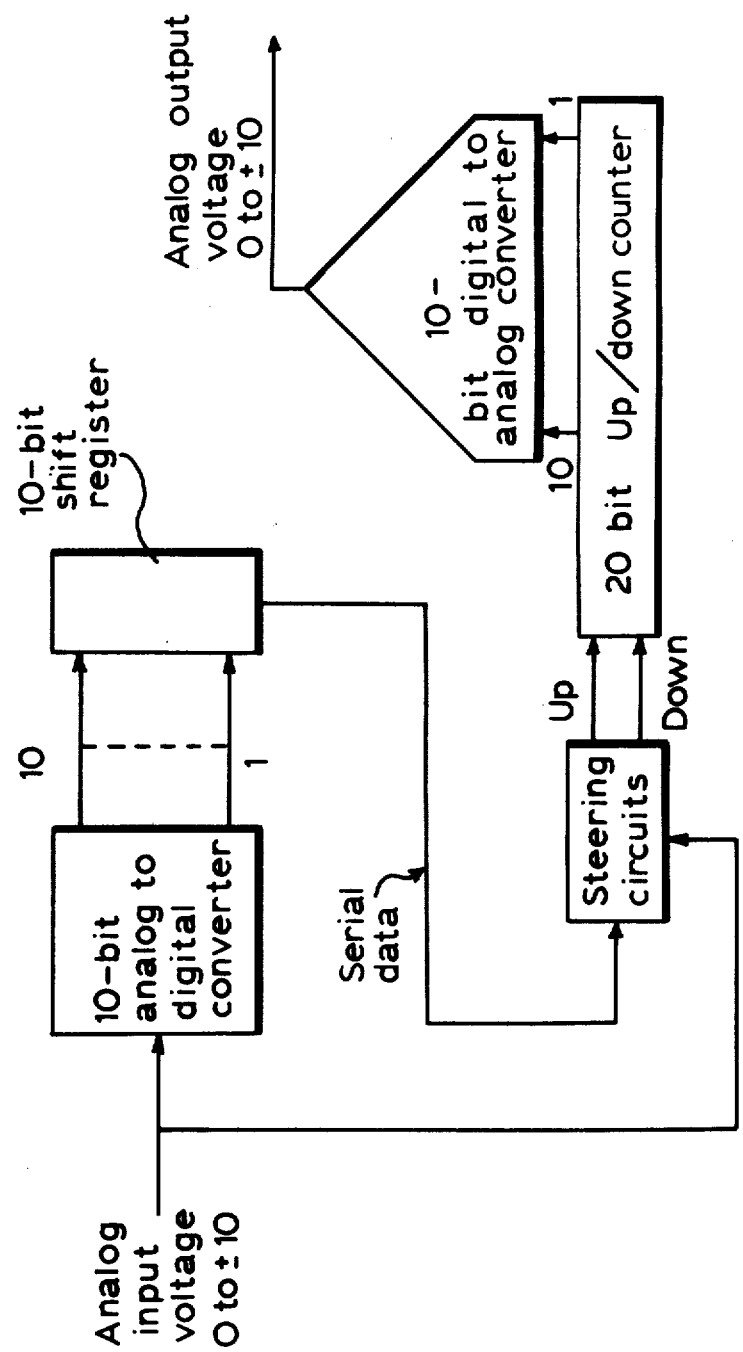
FIG. 4 is a schematic diagram of a clock controlled digital integrator.

More particularly in the embodiment described below, and illustrated in FIG. 4, the analog voltages are $\pm 10$ volts, with the output of the integrator increasing upscale for one polarity of analog input voltage. A change in the polarity of the input voltage causes the output of the integrator to decrease or move downscale. (The device can use a printed circuit board, with wire jumpers to allow for change in the direction of the output voltage; the device can, therefore, be direct or reverse-acting). The analog voltage input is applied to a 10-bit analog-to-digital converter that converts this input voltage to a binary number that is proportional to the magnitude of the input voltage. An input voltage of zero produces a binary number of zero, while an input voltage of $\pm 10$ (the maximum) produces the maximum output of a 10-bit converter, namely a binary number whose decimal equivalent is 1023. The binary number is then transferred in parallel over ten interconnecting wires to a 10-bit shift register capable of storing the 10-bit binary number. The binary number is then shifted out of the shift register as a serial string of pulses over a single wire. The number of pulses shifted can vary between 0 and 1,023, depending on the magnitude of the input voltage converted. The circuit elements are such that the maximum time required for shifting is approximately 2 milliseconds. The string of pulses is then fed through conventional steering circuitry (not shown) and on to a 20-bit up/down counter. The string of pulses can, therefore, either add to the existing count number in the 20-bit up/down counter or it can subtract, depending on the condition of the steering circuitry.

The 20-bit up/down counter can hold 1,000 times more counts than can the shift register. Therefore, if a ±10 volt input is applied to the analog-to-digital converter and is converted to a binary number corresponding to 1,023 counts shifted out of the shift register, then 1,000 shifts of this number of counts will be necessary in order to fill up the 20-bit counter. A 10-bit digital-to-analog converter is attached to the last ten bits of the 20-bit up/down counter, in such manner that if 1,023 counts are shifted from the shift register, then the analog output voltage from the digital-to-analog converter will either increase or decrease 1/1023 of its full range of 10 volts. Thus if the input to the analog-to-digital converter is 10 volts, 1,023 pulses will be shifted from the shift register to the up/down counter every time such a shift is commanded and the output voltage from the digital-to-analog converter will increase approximately 10 millivolts (assuming upcount steering). Approximately 1,000 shift commands will be required for the output voltage from the digital-to-analog converter to move from zero volts linearly to ten volts. The device, therefore, becomes an integrator, with the integration rate proportional to the frequency at which shift commands are entered and to the magnitude of the analog voltage applied to analog-to-digital converter. Thus, if an input voltage to the analog-to-digital converter of five volts is chosen then, upon shift command, only 512 counts will be fed from the shift register to the up/down counter and approximately 2,000 shift commands will be required in order to cause the output voltage from the digital-to-analog converter to move from zero to ten volts. This is equivalent to cutting the integration rate by one-half. The device has time sequencing circuitry of conventional type (not shown) to provide timed pulses and which is connected in such fashion, well known in the art, that each pulse of appropriate polarity serves as a shift command, starting the above described sequence of events.

The steering circuitry is such that the up/down counter will count either up or down depending on the polarity of the input voltage to the analog-to-digital converter. The circuitry is preferably such that there is a positive increasing output voltage from the digital-to-analog converter when the input voltage is positive and vice versa; thus a reversal of the polarity of the input voltage to negative causes the output from the digital-to-analog converter to decrease in value toward zero volts; that is, when the analog input voltage changes from positive to negative polarity, the steering circuitry changes the 20-bit counter from up counter to a down counter.

A small amount of additional circuitry of conventional type (not shown) is required in order to prevent both the shift register and the 20-bit up/down counter from resetting to zero counts when an overflow count is received. For example, if for some reason, the shift register receives from the analog-to-digital converter the count of 1,024, which is one over its capacity, then without the additional circuitry involved, the shift register would ordinarily reset to zero (and a similar situation could occur with the 20-bit up/down counter).

The characteristics of the eliminator of long term bias are such as to reject bias which persists for a period substantially longer than the time constant of the anaerobic filter. For instance when the volume of the recycling anaerobic filter and the expected flow rate therethrough are such that the average expected residence time of the wastewater therein be based on about 17 hours, the time constant (in absence of bacterial activity) will also be about 17 hours and the bias eliminator is preferably designed to reject bias that persists for well over 20 hours (such as 1 or 2 days). It will be understood that, since a reaction occurs in the anaerobic filter (because of the bacterial action) the actual time constant will be less than the average residence time, e.g. the time constant for the same anaerobic filter is about 10 to 15 hours.

A broader aspect of this invention involves the use of the eliminator of long term bias, in combination with an estimating filter, in control circuits for a variety of systems, not only in the anaerobic filter system described in detail herein. Thus it may be used, for instance, in control circuits for various other chemical or physical processes. It is known to use estimating filters in such control circuits.

The estimating filter, which includes an integrator, receives input signals from sensors and at its integrator, generates (from those received signals) an estimate of the present value of a variable of the system. It compares that estimate with a signal from the sensor of that variable and, from that comparison, it generates a difference signal that is combined with said received input signals and fed back to its integrator. A discussion of estimating filters is found, for example, at pages 225 to 252 (e.g. at page 230) of the book by Åström "Introduction to Stochastic Control Theory" published 1970 by Academic Press. If there is an unknown long term bias in one or more of said received input signals (so that, for instance, the resulting sensor-based signal 211a, FIG. 8, has an improper constant bias) the magnitude of the long-term average of the difference signal (such as signal 216 modified by amplifier 60) has to become equal to the magnitude of this improper bias with an opposite sign, the reason for which is as follows: The long-term average of signal 212 has to be zero, because this is the only input to integrator 58 when both switches 76 and 77 are disconnected. That is, if at one time a long-term average of signal 212 is not zero, the output of integrator 58 will keep changing until signal 216 which is fed back to adder 57 brings the long-term average of signal 212 to zero. The bias eliminator acts to avoid this effect. However, the bias eliminator does not reject signal variations whose period is shorter than, or about the same as, the time constant of the system being controlled, which variations are the inputs needed for the control circuit.

The action of the eliminator of long-term bias is related to the fact that in the operation of the estimating filter the known conservation laws are employed. If there were no long term bias, the signal 211 which is the algebraic sum of all the inputs and outputs of organic matter of the system should have a long term average value of zero. That is, at adder 52, the input of organic matter into the system is represented by signal 209 and the outputs are presented by signals 210 and MF and, by the law of conservation of matter, long-term average input and long-term average output should be equal. Accordingly the long term average value of the difference signal 216 from adder 59 should be zero. When there is a long term bias, of magnitude "x", the presence of such bias will cause the long term average value of the difference signal 216 to be $x/K_3$ (where $K_3$ is the gain of amplifier 60). If this is a large value it will vitiate the usefulness of the estimated signal ($oOD_E$) which is the output of the estimating filter. While the foregoing illustration involves the principle of conservation of matter the control circuit may, instead, be used for systems which deal with, say, signals representing energy rather than matter.

The "time constant" is a well-known concept in the design of control circuits. See for instance the discussion of this concept in the book "System Modelling and Control" by Schwarzenbach and Gill (pub. 1978, a Halsted Press Book, John Wiley & Sons) at pages 48 and 58–61. The time constant for responses which are apparently approximately of first order is well understood. For oscillatory responses the time constant is to be taken on the basis of the time it takes for the response to become substantially settled.

Preferably integrators 32 (FIG. 7), 58 (FIG. 8), 96 (FIG. 9), 109 (FIG. 10), 122 (FIG. 11), and 128 (FIG. 12) are clock-controlled digital integrators of the same type as integrator 79. In the circuits used for intermittently correcting the outputs of the clock-controlled digital integrator (such as the circuit containing switch 49 or 51 of FIG. 7) the function of the high gain amplifier (such as amplifier 48) may be accomplished by suitable circuiting that speeds up the integration time of the clock-controlled digital integrator.

In the illustrated preferred embodiment the signals are transmitted electrically. However, the invention is also applicable to pneumatic, mechanical, hydraulic or other signal means for transmitting information. In almost all control systems some combination of these types of signals will be used. However, use of any other type of signal transmission, compatible with the process and equipment in use is within the scope of the invention.

In the illustrated embodiment many of the signals are processed by analog computing devices. It will be understood that digital computing may be used in place of all or a portion of the analog elements used to calculate the required control signals based on measured process parameters as well as set points supplied to the computer.

It will be understood that in the broader scope of the invention all or part of the illustrated control modes may be replaced by other modes, such as proportional, proportional-integral, proportional-derivative, or proportional-integral-derivative.

The various transducing means used to measure parameters which characterize the process and the various signals generated thereby may take a variety of forms or formats. For example, the control elements of the system can be implemented using electrical analog, digital electronic, pneumatic, hydraulic, mechanical or other similar types of equipment or combinations of one or more of such equipment types. Likewise, the format of the various signals can be modified substantially in order to accommodate signal format requirements of the particular installation, safety factors, the physical characteristics of the measuring or control instruments and other similar factors. For example, a raw flow measurement signal produced by a differential pressure orifice flow meter would ordinarily exhibit a generally proportional relationship to the square of the actual flow rate. Other measuring instruments might produce a signal which is proportional to the measured parameter, and still other transducing means may produce a signal which bears a more complicated, but known, relationship to the measured parameter. In addition, all signals could be translated into a "suppressed zero" or other similar format in order to provide a "live zero" and prevent an equipment failure from being erroneously interpreted as a "low" or "high" measurement or control signal. Regardless of the signal format or the exact relationship of the signal to the parameter which it represents, each signal representative of a measured process parameter or representative of a desired process value will bear a relationship to the measured parameter or desired value which permits designation of a specific measured or desired value by a specific signal value. A signal which is representative of a process measurement or desired process value is therefore one from which the information regarding the measured or desired value can be readily retrieved regardless of the exact mathematical relationship between the signal units and the measured or desired process units.

In a broader aspect of the invention, the control technique described herein may be used not only for anaerobic filters but also for other anaerobic methanogenic backmixing reactor vessels in which, like the recycling anaerobic filters, a bed of the methanogenic bacteria is substantially retained in the anaerobic reactor vessel while the waste water passes upwards through that bed, the effluent from the vessel having a much lower bacterial concentration than is present in the bed of methanogenic bacteria. One such reactor is that described as the "Upflow Sludge Blanket (USB) Reactor" in the article by G. Lettinga et al entitled "Use of the Upflow Sludge Blanket (USB) Reactor Concept for Biological Wastewater Treatment, especially for Anaerobic Treatment" in Biotechnology and Bioengineering Vol. XII No. 4 April 1980 pages 699–734; this reactor and its operation are also described in the article by G. Lettinga entitled "Direct Anaerobic Treatment Handles Wastes Effectively" in the journal Industrial Wastes for January/February, 1979 pages 18–24, 40 and 41, German Offenlegungschrifte 2920978 and 2921070 both published 29.11.79, the article by Lettinga et al entitled "Anaerobic Treatment of Methanolic Wastes" in the journal "Water Research" vol. 13 (1979) pages 725 to 737 and the article entitled "Feasibility of Anaerobic Digestion for the Purification of Industrial Waste Waters" by Lettinga in Documentation-Europe Sewage & Refuse Symposium EAS, 4th, Muniche 1978 (pub. by Abwassertechnische Vereinigung St. Augustin, German Federal Republic 5205) pages 226–256, the paper on "The Elimination of Organic Wastes from Surface Water" given by Th. M. van Bellegem at the 13th International TNO Conference at Rotterdam 27–28 March 1980 (paper available from Netherlands Organization for Applied Scientific Research TNO) and the article entitled "A Pilot Scale Anaerobic Upflow Reactor Treating Distillery Wastewaters" by Plpyn et al in Biotechnology Letters 1, pages 495–500 (1979). Another such reactor is that in which the bacteria are attached to support particles, such as described in the article by M. S. Switzenbaum et al entitled "Anaerobic Attached—Film Expanded-Bed Reactor Treatment" in Journal WPCF Vol. 52 No. 7 (July 1970) pages 1953-1965, the articles by B. Atkinson et al entitled "Process Intensification Using Cell Support Systems" (in Process Biochemistry, May 1980 pages 24–32) and "Biological Particles of Given Size, Shape and Density for Use in Biological Reactors" (in Biotechnology and Bioengineering Vol. XXI pages 193–200 (1979) and in published U.K. Patent Application GB 2006 181 A published May 2, 1979. In both these types of reactors the bacteria are present on relatively large particles or flowable aggregates of such size and density that they have a high sedimentation velocity in still water such that even at high loading conditions (such as hydraulic retention times of less than 2 days, e.g. 1 day or less) the concentration of bacterial suspended solids in the effluent at the top of the reactor is relatively low, such as less than 0.05 gram (e.g. 0.01 gram) of bacterial suspended solids per gram of COD in the feed to the reactor, and the bacteria are retained in the reactor for long periods of time (their average residence time in the reactor being, for instance, over 10 days such as about 30 or 100 days or more).

The embodiments of the invention in which an exclusive property or privilege is claimed are defined as follows:

1. An anaerobic reactor system comprising
an anaerobic bacterial reactor adapted to convert organic compounds in an aqueous wastewater stream into methane and carbon dioxide, said reactor comprising a vessel containing a backmixed bed of methanogenic bacteria which are so aggregated that said bed is substantially retained in said vessel while the wastewater passes upwards through that bed,
means for feeding said aqueous organic wastewater stream to said anaerobic reactor,
means for withdrawing an aqueous liquid effluent stream from said anaerobic reactor,
means for withdrawing a gaseous stream comprising methane for said anaerobic reactor,
means for measuring the rate at which oxygen demand is fed to said anaerobic reactor in said waste stream and for generating a signal which is representative of said measured feed oxygen demand,
means for measuring the rate of flow of methane in said gaseous stream and for generating a signal representative of said measured methane flow rate,
an estimating filter, receiving said signals, for estimating the oxygen demand in said effluent stream and for generating a signal representative of said estimated effluent oxygen demand, and
means, responsive to said signal for estimated effluent oxygen demand, for controlling the rate at which said aqueous organic waste stream is fed to said anaerobic reactor.

2. A system as in claim 1 which comprises
means for measuring the oxygen demand in said effluent stream and for generating a signal which is representative of said measured effluent oxygen demand, and in which
said estimating filter receives said measured effluent oxygen demand signal, compares said measured signal with said estimated signal to obtain a difference signal, and modifies said estimated signal by feedback of said difference signal.

3. A system as in claim 1 comprising an eliminator of long term bias that may be present in one or more of the measurement-representative signals, said eliminator comprising a high pass filter through which said measurement-representative signals are transmitted to said estimating filter, said high pass filter rejecting bias which persists for a period substantially longer than the time constant of the system.

4. A system as in claim 2 comprising an eliminator of long term bias that may be present in one or more of the measurement-representative signals, said eliminator comprising a high pass filter through which said measurement-representative signals are transmitted to said estimating filter, said high pass filter rejecting bias which persists for a period substantially longer than the time constant of the system.

5. A system as in claim 1 comprising
means for feeding a set point signal to said controlling means,
a storage tank from which said waste stream is fed to said anaerobic reactor,
means for measuring the level of aqueous waste in said tank and
means for modifying said set point signal in response to the value of said measured level.

6. A system as in claim 5 in which said level-measuring means generates a signal which is representative of said measured level, and said system comprises
means for measuring the rates of inflow and outflow of said aqueous organic waste into and out of said tank and for generating a signal representative of the difference between inflow and outflow, and
said modifying means comprises an estimating filter, receiving said inflow-outflow difference signal and said measured level signal, for estimating the level in said tank and for generating a signal representative of said estimated level.

7. An anaerobic reactor system comprising
a recycling anaerobic filter for converting organic compounds in an aqueous watewater stream into methane and carbon dioxide by the action of methanogenic bacteria in said anaerobic filter,
means for feeding said aqueous organic wastewater stream to said anaerobic filter,
means for withdrawing an aqueous liquid effluent stream from said anaerobic filter,
means for withdrawing a gaseous stream comprising methane from said anaerobic filter,
means for measuring the rate at which oxygen demand is fed to said anaerobic filter in said waste stream and for generating a signal which is representative of said measured feed oxygen demand,
means for measuring the rate of flow of methane in said gaseous stream and for generating a signal representative of said measured methane flow rate,
an estimating filter, receiving said signals, for estimating the oxygen demand in said effluent stream and for generating a signal representative of said estimated effluent oxygen demand, and
means, responsive to said signal for estimated effluent oxygen demand, for controlling the rate at which said aqueous organic waste stream is fed to said anaerobic filter.

8. A system as in claim 7 which comprises
means for measuring the oxygen demand in said effluent stream and for generating a signal which is representative of said measured effluent oxygen demand, and in which
said estimating filter receives said measured effluent oxygen demand signal, compares said measured signal with said estimated signal to obtain a difference signal, and modifies said estimated signal by feedback of said difference signal.

9. A system as in claim 7 comprising an eliminator of long term bias that may be present in one or more of the measurement-representative signals, said eliminator comprising a high pass filter through which said measurement-representative signals are transmitted to said estimating filter, said high pass filter rejecting bias which persists for a period substantially longer than the time constant of the system.

10. A system as in claim 8 comprising an eliminator of long term bias that may be present in one or more of the measurement-representative signals, said eliminator comprising a high pass filter through which said measurement-representative signals are transmitted to said estimating filter, said high pass filter rejecting bias which persists for a period substantially longer than the average residence time of said wastewater in said anaerobic filter.

11. A system as in claim 7 comprising means for feeding a set point signal to said controlling means, a storage tank from which said waste stream is fed to said anaerobic filter, means for measuring the level of aqueous waste in said tank and means for modifying said set point signal in response to the value of said measured level.

12. A system as in claim 11 in which said level-measuring means generates a signal which is representative of said measured level, and said system comprises means for measuring the rates of inflow and outflow of said aqueous organic waste into and out of said tank and for generating a signal representative of the difference between inflow and outflow, and said modifying means comprises an estimating filter, receiving said inflow-outflow difference signal and said measured level signal, for estimating the level in said tank and for generating a signal representative of said estimated level.

* * * * *